United States Patent [19]

Fenical et al.

[11] Patent Number: 5,473,057
[45] Date of Patent: Dec. 5, 1995

[54] ELEUTHEROBIN AND ANALOGS THEREOF

[75] Inventors: William H. Fenical, Del Mar; Paul R. Jensen, San Diego, both of Calif.; Thomas Lindel, Muenster, Germany

[73] Assignee: The Regents of the University of California, Oakland, Calif.

[21] Appl. No.: 336,518

[22] Filed: Nov. 9, 1994

[51] Int. Cl.[6] .......................... C07H 15/00; C07H 17/00
[52] U.S. Cl. ...................... 536/17.3; 536/18.1; 536/18.2
[58] Field of Search ............................... 536/17.3, 18.1, 536/18.2; 548/300.1, 311.1, 311.4, 315.4, 323.5, 324.1, 326.1, 335.1, 341.1, 341.5, 432, 433, 448

[56] References Cited

PUBLICATIONS

Kenard et al., "Chemical Studies of Marine Invertebrates. IV.[1a] Terpenoids LXII.[1b] Eunicellin, a Diterpenoid of the Gorgonian *Eunicella Stricta*. X–ray Diffraction Analysis of Eunicellin Dibromide," *Tet. Ltrs.*, No. 24, pp. 2879–2884, 1968.

D'Ambrosio et al., "189.Sarcodictyin A and Sarcodictyin B, Novel Diterpenoidic Alcohols Esterified by (E)–N(1)–Methylurocanic Acid. Isolation from the Mediterranean Stolonifer *Sarcodictyon roseum*," *Helvetica Chimica Acta*–vol. 70, pp. 2019–2027 (1987).

D'Ambrosio et al., "105.Isolation from the Mediterranean Stoloniferan Coral *Sarcodictyon roseum* of Sarcodictyin C, D, E, and F, Novel Diterpenoidic Alcohols Esterifieid by (E)–or (Z)–N(1)–Methylurocanic Acid. Failure of the Carbon–Skeleton Type as a Classification Criterion)", *Helvetica Chimica Acta*, vol. 71, pp. 964–977 (1988).

Lin et al., "The Valdivones, Anti–inflammatory Diterpene Esters from the South African Soft Coral *Alcyonium valdivae*," *Tetrahedron*, vol. 49, No. 36, pp. 7977–7984 (1993).

Kazlauskas et al., "Two New Diterpenes Related to Eunicellin from a Cladiella Species (Soft Coral)," *Tetr. Ltrs.*, No. 52, pp. 4643–4646 (1977).

*Primary Examiner*—Nathan M. Nutter
*Attorney, Agent, or Firm*—Poms, Smith, Lande & Rose

[57] ABSTRACT

Eleutherobin is a glycosylated diterpene which has the structural formula:

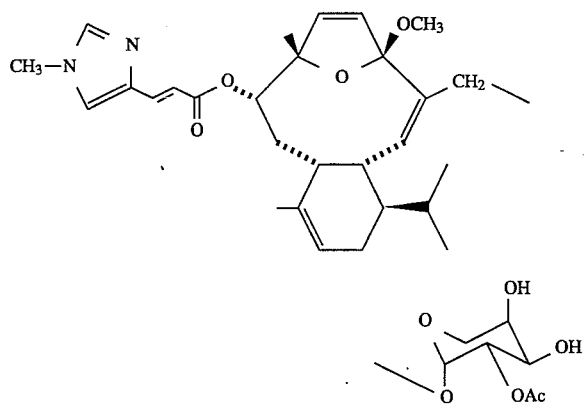

Eleutherobin is a cytotoxic agent which is toxic to carcinoma cancer cells. Analogs of eleutherobin are also disclosed.

4 Claims, 3 Drawing Sheets

5,473,057

ELEUTHEROBIN AND ANALOGS THEREOF

BACKGROUND OF THE INVENTION

This invention was made with Government support under Grant No. CA50750, awarded by the National Cancer Institute. The Government has certain rights in this invention.

1. Field of the Invention

The present invention relates generally to pharmacologically active compounds which are isolated from marine life, such as sea whips, sea fans and soft corals. More particularly, the present invention relates to such naturally occurring marine products and analogs thereof which include a diterpene core of the eunicellan class.

2. Description of Related Art

There has been and continues to be a great deal of interest in isolating pharmacologically active compounds from marine sources. Numerous useful compounds have been isolated from marine organisms ranging from simple bacteria to complex plants and animals. The compounds themselves also range from relatively simple compounds to extremely complex compounds with the range of pharmacological utility also being quite large and varied. Sea fans, sea whips and soft corals have been an especially fertile source of compounds which are pharmacologically active.

Eunicellin is a naturally occurring marine compound which was first isolated from the gorgonian *Eunicella stricta* in 1968 (O. Kennard, D. G. Watson, L. Riva de Sanservierine, B. Tursch, R. Bosmans, C. Djerassi, *Tetrahedron Lett.* 1968, 2879–2883). Eunicellin is a diterpene compound which has the following chemical structure

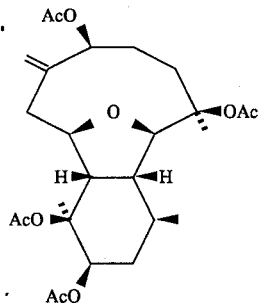

No bioactivity for eunicellin has been reported.

Another naturally occurring marine compound is Sarcodictyin A. Sarcodictyin A was first isolated in the late 1980's from the mediterranean stolonifer *Sarcodictyon roseum* (M. D'Ambrosio, A. Guerriero, F. Pietra, Helv. Chim. Acta 1987, 70,2019–2027; and M. D'Ambrosio, A. Guerriero, F. Pietra, ibid. 1988, 71, 964–976). The chemical structure of Sarcodictyin A is

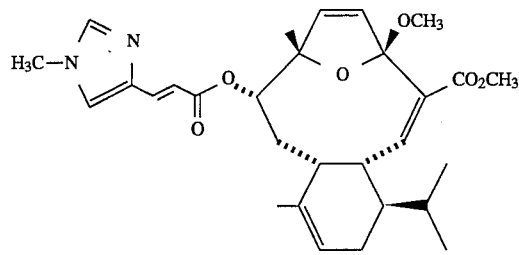

No bioactivity for Sarcodictyin A has been reported.

The valdivones are a group of marine compounds which were initially isolated from the South African soft coral *Alcyonium valdivae* in 1993 (Y. Lin, C. A. Bewley, D. J. Faulkner, *Tetrahedron* 1993, 49, 7977–7984). Valdivone A and Valdivone B are two examples of this type of compound. The chemical formulas for these two compounds are

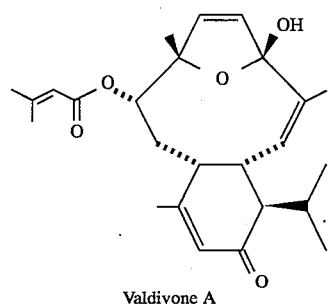

Valdivone A

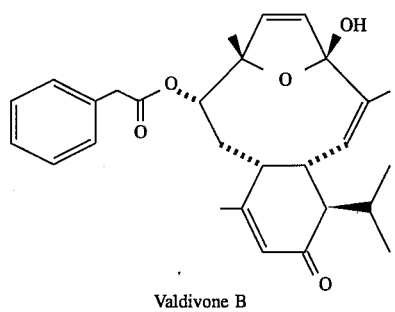

Valdivone B

Both Valdivone A and Valdivone B have been shown to possess anti-inflammatory activity.

The above mentioned compounds are a few examples of the many different types of materials which have been isolated as a result of the many scientific efforts to recover useful chemicals from marine life. These efforts continue today and will continue into the future as new chemical compounds are isolated, identified and found to be pharmacologically useful.

SUMMARY OF THE INVENTION

In accordance with the present invention a new compound has been isolated from the Indian Ocean soft coral *Eleuth-*

*erobia cf. albiflora.* *E. albiflora* is a red-colored cnidarian relatives of which are located throughout the world in locations such as Western Australia, the Pacific and Indian Oceans.

The isolated compound has been given the name "Eleutherobin" and has been found to have the following chemical formula:

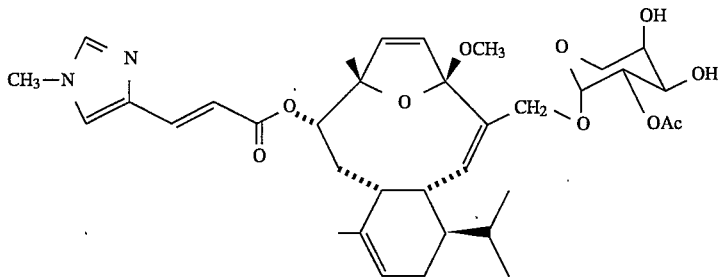

Eleutherobin has been tested for pharmacological activity and found to be an effective cytotoxin.

As a feature of the present invention, analogs of eleutherobin are disclosed which have the general formula:

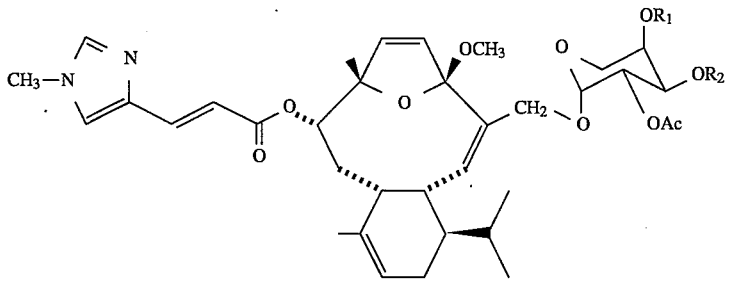

where $R_1$ and $R_2$ are hydrogen or acyl residues having from 1 to 6 carbon atoms. These closely related analogs are also expected to exhibit cytotoxic activity.

The above described and many other features and attendant advantages of the present invention will become better understood by reference to the following detailed description when taken in conjunction with the accompanying drawings.

DETAILED DESCRIPTION OF THE INVENTION

Figure 1:
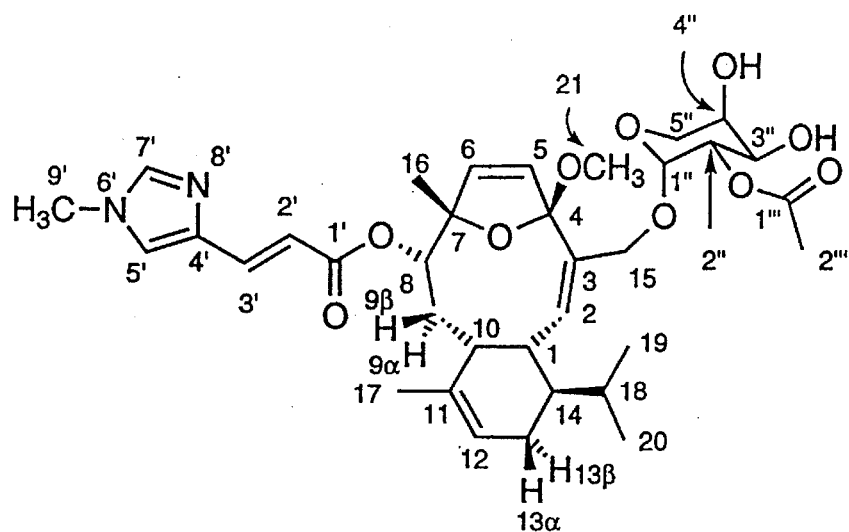
FIG. 1 is the formula for eleutherobin showing the atom labels.

The present invention is based on the discovery of a specific glycosylated diterpene which was initially isolated from *Eleutherobia cf. albiflora.* *E. albiflora* is a red-colored cnidarian which is located in Western Australia off the North West Cape near Exmouth. The glycosylated diterpene has been given the name "Eleutherobin" and has been identified as having the following formula:

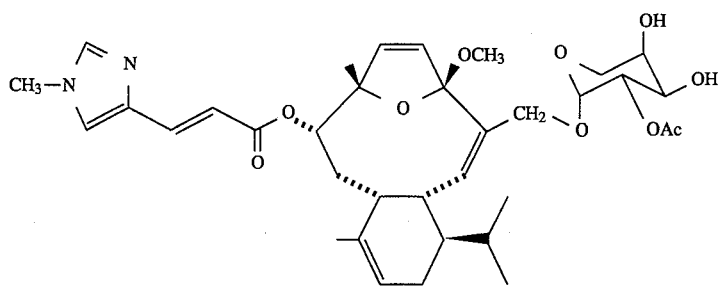

The molecular formula of eleutherobin as determined by high resolution FAB mass spectrometry (HRFABMS) is $C_{35}H_{48}N_2O_{10}$, indicating 13 degrees of unsaturation. As in the case of other natural products, the intensity of the molecular ion peak was small, while on adding sodium, a strong signal corresponding to the $[M+Na]^+$ ion was detected. The physical and spectroscopic data for eleutherobin are set forth in Tables 1–4.

TABLE 1

Eleutherobin yield: 15 mg from 150 g freeze dried soft coral (0.01%)
TLC: $R_f$ + 0.33 (chloroform/methanol (9:1))
$[\alpha]D^{25} = -49.3°$ (c = 3.0, methanol)
HRFABMS: $[C_{35}H_{48}N_2O_{10}Na]^+$ calc. 679.3207    obs. 679.3174 (−4.8 ppm)
IR (NaCl, neat): v = 3360 $cm^{-1}$, 2960, 2922, 2856, 1722, 1657, 1450, 1372, 1243, 1152, 1055.
UV (methanol): $\lambda_{max}$ (log ε) = 290 nm (3.824).

TABLE 2

NMR spectral data for eleutherobin

| label | $^{13}C$ NMR[a] | $^1H$ NMR[b] | HMBC correlations[c] |
|---|---|---|---|
| 1 | 34.3(d) | 3.96(m) | none |
| 2 | 137.4(d) | 5.56(d, 9.2Hz) | C-4, C-14, C-15 |
| 3 | 132.8(s) | | |
| 4 | 115.9(s) | | |
| 5 | 131.0(d) | 6.12(d, 5.9 Hz) | C-4, C-6, C-7 |
| 6 | 133.7(d) | 6.09(d, 5.9 Hz) | C-4, C-5, C-7 |
| 7 | 89.9(s) | | |
| 8 | 81.5(d) | 4.82(d, 7.7 Hz) | C-6, C-7, C-16, C-29, C-1' |
| 9 | 31.5(t) | 1.39(m) | C-1, C-7 |
|   |          | 1.61(m) | C-1, C-8, C-10 |
| 10 | 38.7(d) | 2.61(m) | none |
| 11 | 134.2(s) | | |
| 12 | 121.3(d) | 5.28(m) | C-17 |
| 13 | 24.5(t) | 1.98(m) | none |
|    |         | 2.32(m) | none |
| 14 | 42.4(d) | 1.23(m) | none |
| 15 | 69.1(t) | 3.88(d, 12.4 Hz) | C-2, C-3, C-4, C-1" |
|    |         | 4.31(d, 12.4 Hz) | C-2, C-3, C-1" |
| 16 | 24.3(q) | 1.45(s) | C-7, C-8 |
| 17 | 21.9(q) | 1.52(s) | C-11, C-12 |
| 18 | 29.1(d) | 1.57(m) | none |
| 19 | 20.5(q) | 0.97(d, 6.5 Hz) | C-14, C-18, C-20 |
| 20 | 22.2(q) | 0.93(d, 6.5 Hz) | C-14, C-18, C-19 |
| 21 | 49.6(q) | 3.22(s) | C-4 |
| 1' | 166.7(s) | | |
| 2' | 115.9(d) | 6.57(d, 15.5 Hz) | C-1, C-4' |
| 3' | 136.4(d) | 7.55(d, 15.5 Hz) | C-1', C-2', C-4', C-5' |
| 4' | 138.4(s) | | |
| 5' | 122.9(d) | 7.10(s) | C-4', C-7' |
| 7' | 139.5(d) | 7.48(s) | C-4', C-5' |
| 9' | 33.6(q) | 3.72(s) | C-5', C-7' |
| 1" | 93.4(d) | 4.91(d, 3.7 Hz) | C-3", C-5" |
| 2" | 71.8(d) | 4.99(dd, 9.8, 3.7 Hz) | C-3", C-1''' |
| 3" | 68.1(d) | 4.03(dd, 9.8, 3.7 Hz) | C-2" |
| 4" | 69.5(d) | 3.99(m) | C-3" |
| 5" | 62.1(t) | 3.70(d, 11.9 Hz) | C-1", C-3" |
|    |         | 3.83(d, 11.9 Hz) | C-1" |
| 1''' | 171.4(s) | | |
| 2''' | 21.0(q) | 2.11(s) | C-1" |

[a]acquired at 50 MHz in $CDCl_3$
[b]acquired at 500 MHz in $CDCl_3$
[c]acquired at an effective J = 8 Hz

TABLE 3

Table of NMR spectral data for eleutherobin

| label | $^{13}C$ NMR | $^1H$ NMR |
|---|---|---|
| 1 | 34.5 | 3.89(m) |
| 2 | 135.2 | 5.40(d, 9.3 Hz) |
| 3 | 133.0 | |
| 4 | 116.0 | |
| 5 | 130.8 | 6.08(d, 5.5 Hz) |
| 6 | 133.9 | 6.27(d, 5.5 Hz) |
| 7 | 89.5 | |
| 8 | 80.9 | 4.66(d, 5.7 Hz) |
| 9 | 30.7 | 1.32(m) |
|   |      | 1.48(m) |
| 10 | 38.5 | 2.44(m) |

TABLE 3-continued

Table of NMR spectral data for eleutherobin

| label | $^{13}$C NMR | $^1$H NMR |
|---|---|---|
| 11 | 133.9 | |
| 12 | 121.1 | 5.28(m) |
| 13 | 23.9 | 1.95(m) |
|  |  | 2.27(m) |
| 14 | 42.2 | 1.23(m) |
| 15 | 67.8 | 3.77(d, 12.0 Hz) |
|  |  | 4.17(d, 12.0 Hz) |
| 16 | 23.9 | 1.37(s) |
| 17 | 21.6 | 1.47(s) |
| 18 | 28.9 | 1.46(m) |
| 19 | 20.2 | 0.93(d, 4.5 Hz) |
| 20 | 22.1 | 0.92(d, 4.5 Hz) |
| 21 | 49.3 | 3.09(s) |
| 1' | 166.3 | |
| 2' | 113.8 | 6.35(d, 11.0 Hz) |
| 3' | 138.1 | 7.53(d, 11.0 Hz) |
| 4' | 137.3 | |
| 5' | 125.0 | 7.57(s) |
| 7' | 140.2 | 7.69(s) |
| 9' | 34.2 | 3.66(s) |
| 1" | 93.2 | 4.70(d, 3.4 Hz) |
| 2" | 70.9 | 4.82(dd, 9.7, 3.4 Hz) |
| 3" | 66.2 | 3.78(dd, 9.7, 3.4 Hz) |
| 4" | 68.5 | 3.76(m) |
| 5" | 63.2 | 3.44(dd, 12.0, 2.3 Hz) |
|  |  | 3.60(d, 12.0 Hz) |
| 1''' | 170.1 | |
| 2''' | 21.0 | 2.01(s) |

$^a$acquired at 50 MHz in DMSO-d$_6$
$^b$acquired at DMSO-d$_6$

TABLE 4

Table of proton-proton correlations for eleutherobin
(500 MHz, chloroform-d$_1$, J = 8 Hz)

| label | 1H NMR | COSY correlations | NOESY correlations |
|---|---|---|---|
| 1 | 3.96(m) | H-2, H-10 | H-1, H-2, H-8, H-10, H-14, H-19 |
| 2 | 5.56(d, 9.3 Hz) | H-1 | H-1, H-13β, H-14 |
| 5 | 6.12(d, 5.8 Hz) | H-6 | H-6, H-15β, H-21 |
| 6 | 6.09(d, 5.8 Hz) | H-5 | H-16, H-2''' |
| 8 | 4.82(d, 7.7 Hz) | H-9α | H-1, H-10, H-16 |
| 9 | 1.39(m) | H-8, H-9β, H-10 | H-9β |
|  | 1.61(m) | H-9α | H-9α, H-10 |
| 10 | 2.61(m) | H-1, H-9α | H-1, H-8, H-18, H-19 |
| 12 | 5.28(m) | H-13α, H-17 | H-13α, H-13β, H-17 |
| 13 | 1.98(m) | H-12, H-13β, H-17 | H-12, H-13β, H-20 |
|  | 2.32(m) | H-13α, H-14, H-17 | H-2, H-13α, H-14 |
| 14 | 1.23(m) | H-1, H-13β, H-17 | H-1 |
| 15 | 3.88(d, 12.4 Hz) | H-15β | H-2, H-15β, H-1" |
|  | 4.31(d, 12.4 Hz) | H-15α | H-15α |
| 16 | 1.45(s) | none | H-6, H-8, H-21 |
| 17 | 1.52(s) | H-12, H-13β, H-13β | H-1, H-12, H-17, H-19 |
| 18 | 1.57(m) | H-14, H-19, H-20 | H-10, H-14, H-19, H-20 |
| 19 | 0.97(d, 6.5 Hz) | H-18 | H-10 |
| 20 | 0.93(d, 6.5 Hz) | H-18 | H-9β, H-13α, H-14 |
| 21 | 3.22(s) | none | H-8, H-16 |
| 2' | 6.57(d, 15.5 Hz) | H-3' | H-3' |
| 3' | 7.55(d, 15.5 Hz) | H-2' | H-2' |
| 5' | 7.10(s) | none | H-9' |
| 7' | 7.48(s) | none | none |
| 9' | 3.72(s) | none | none |
| 1" | 4.91(d, 3.7 Hz) | H-2" | H-2, H-15α, H-2" |
| 2" | 4.99(dd, 9.8, 3.7 Hz) | H-1", H-3" | H-1", H-3" |
| 3" | 4.03(dd, 9.8, 3.7 Hz) | H-2", H-4" | H-2" |
| 4" | 3.99(m) | H-3" | H-5"α, H-5"β, H-19 |
| 5" | 3.70(d, 11.9 Hz) | H-4", H-5"β | H-4"α, H-5"β |
|  | 3.38(d, 11.9 Hz) | H-4", H-5"α | H-4", H-5"α |
| 2''' | 2.11(s) | none | none |

Figure 2:
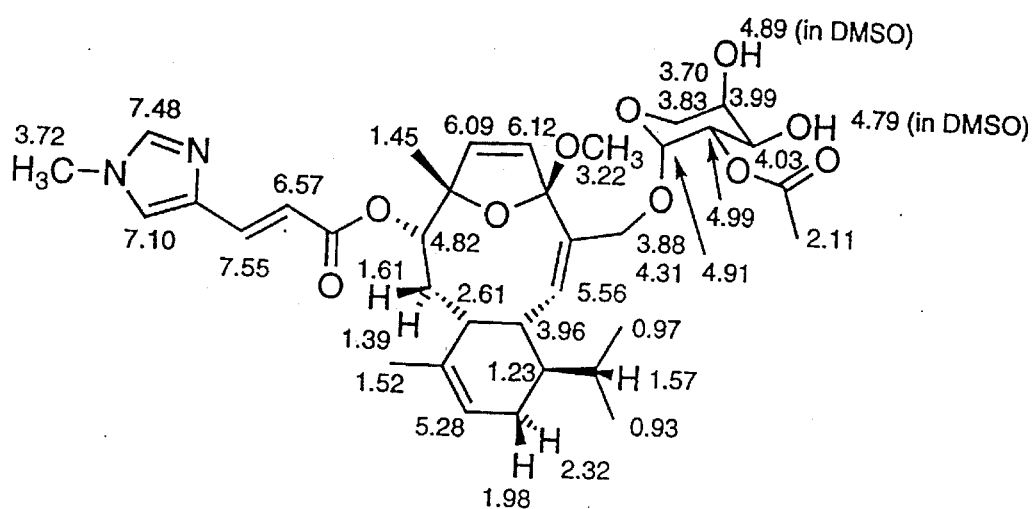
FIG. 2 is the formula for eleutherobin showing the $^1$H NMR chemical shifts at 500 MHz in chloroform-$d_1$.
Figure 3:
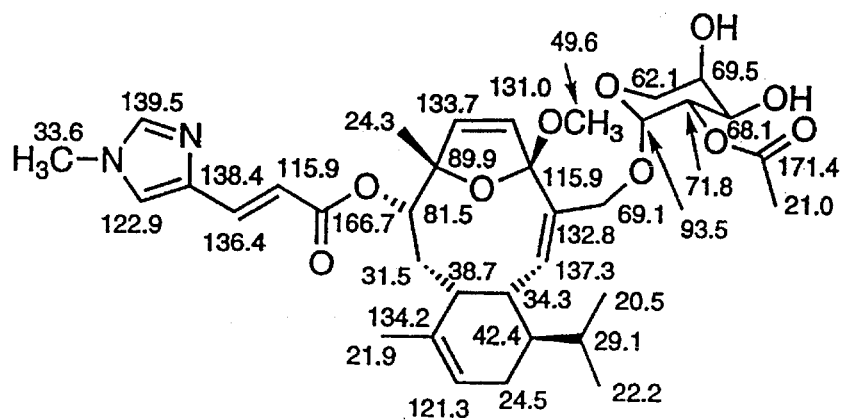
FIG. 3 is the formula for eleutherobin showing the $^{13}$C NMR chemical shifts at 50 MHz in chloroform-$d_1$.

Two sets of NMR spectra are presented in the above Tables (in chloroform-d$_1$ and in DMSO-d$_6$) because of overlapping signals in the $^{13}$C NMR spectrum. The chemical shifts discussed below in the following are with reference to chloroform-d$_1$. Due to the presence of two carbonyl and 11 other olefinic carbon atoms, one of the nitrogen atoms is part of a double bond while the other one is aliphatic, resulting in eight double bonds and thereby a pentacyclic molecule. The distortionless enhanced polarization transfer (DEPT) spectrum shows 7 quaternary, 17 tertiary, 4 secondary, and 7 primary carbon atoms, counting for 46 hydrogen atoms. The remaining two protons are attached to heteroatoms. The chemical shifts for $^1$H NMR and $^{13}$C NMR are set forth in FIGS. 2 and 3, respectively.

Except for the signal at δ=5.28 ppm, all olefinic signals show simple spin systems. An α,β-unsaturated carbonyl moiety is indicated by the chemical shifts of the two coupling (J=15.5 Hz) protons showing resonance at δ=6.57 ppm and δ=7.55 ppm and by the corresponding $^{13}$C NMR chemical shifts at δ=115.9 ppm and δ=136.4 ppm. The signals at δ=6.09 ppm and at δ=6.12 ppm couple with each other (J=5.9 Hz) and result from protons attached to a Z-configuration double bond embedded in a ring. The doublet at δ=5.56 ppm corresponds to a proton attached to a trisubstituted double bond and couples with an aliphatic methine proton. The other olefinic protons at δ=7.10 ppm and at δ=7.48 ppm show singlet resonances. The variety of signals between δ=3.70 ppm and δ=5.00 ppm, together with the fact that 8 oxygen atoms in addition to the carbonyl oxygen atoms are present, indicates that the molecule contains a sugar moiety. This is further confirmed by the $^{13}$C NMR spectrum which shows six resonances between δ=60 ppm and δ=100 ppm, including acetal carbon at δ=93.4 ppm. The singlets at β=3.22 ppm and at δ=3.72 ppm result from a methylated tertiary nitrogen and a methoxy group. The $^{13}$C NMR spectrum in DMSO-d$_6$ shows two different signals at δ=113.8 ppm (olefinic CH) and at δ=116.0 ppm (C, acetal carbon) whereas in chloroform-d$_1$, those signals are overlapping at δ=115.9 ppm.

The constitution of eleutherobin was established by extensive 2D NMR spectroscopy, including correlation spectroscopy (COSY), heteronuclear multiple bond quantum coherence (HMQC) and heteronuclear multiple bond correlation (HMBC) methods. The structure is secured by more than 60 HMBC correlations, observed in two different solvents (chloroform-d$_1$ and DMSO-d$_6$). The assignment of the two olefinic protons showing signals at δ=6.09 ppm and at δ=6.12 ppm is possible because of an HMBC correlation between H-8 and C-6. The position of the oxygen bridge between C-4 and C-7 forming the dihydrofuran moiety can unambiguously be concluded from the HMBC and COSY correlations established part of the structure, from the sum formula, and from the chemical shifts shown by C-4 (δ=115.9 ppm) and by C-7 (δ=89.9 ppm). The connections between the diterpene core and the urocanic acid and pentosopyranose units are established via HMBC correlations between H-8 and C-1' resp. H-15a, H-15b and C-1". The 2"-position of the acetoxy group is established by the chemical shift of H-2" (δ=4.99 ppm) and C-2" (δ=71.8 ppm) as well as by the HMBC correlation between H-2" and the carbonyl atom C-1'". The atom labels for eleutherobin are set forth in FIG. 1.

Figure 4:
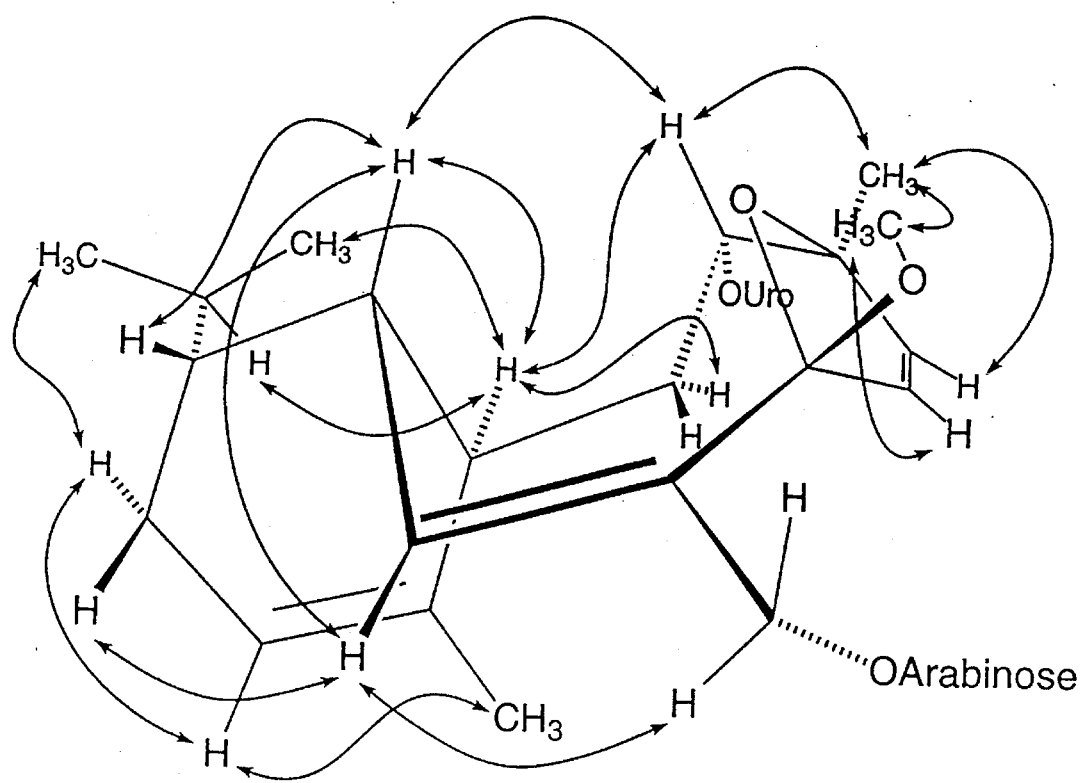
FIG. 4 is a structural diagram showing the nuclear Overhauser enhancement (NOE) correlations of the terpene core of eleutherobin at 500 MHz in chloroform-$d_1$.

Eleutherobin features five carbon-carbon double bonds, one of which is part of an N-methyl imidazole ring. The E-configuration of the double bond between C-2' and C-3' can be concluded from the coupling constants of the attached protons (J=15.5 Hz) and from the wavelength of the UV absorption (λ=290 nm, methanol) of eleutherobin (1). A Z-conformation urocanic acid would have a maximum UV absorption at about a λ270 nm). The trisubstituted double bond between C-2 and C-3 must have a Z-configuration for steric reasons. This structure was also confirmed by NOE correlations as best shown in FIG. 4.

Eleutherobin may be prepared by various routes including: (1) isolation from various Eleutherobia species such as *Eleutherobia cf. albiflora and E. cf. grayi;* (2) reduction and glycosylation of sarcodictyin A; and (3) total synthesis from conventional starting materials.

Figure 5:
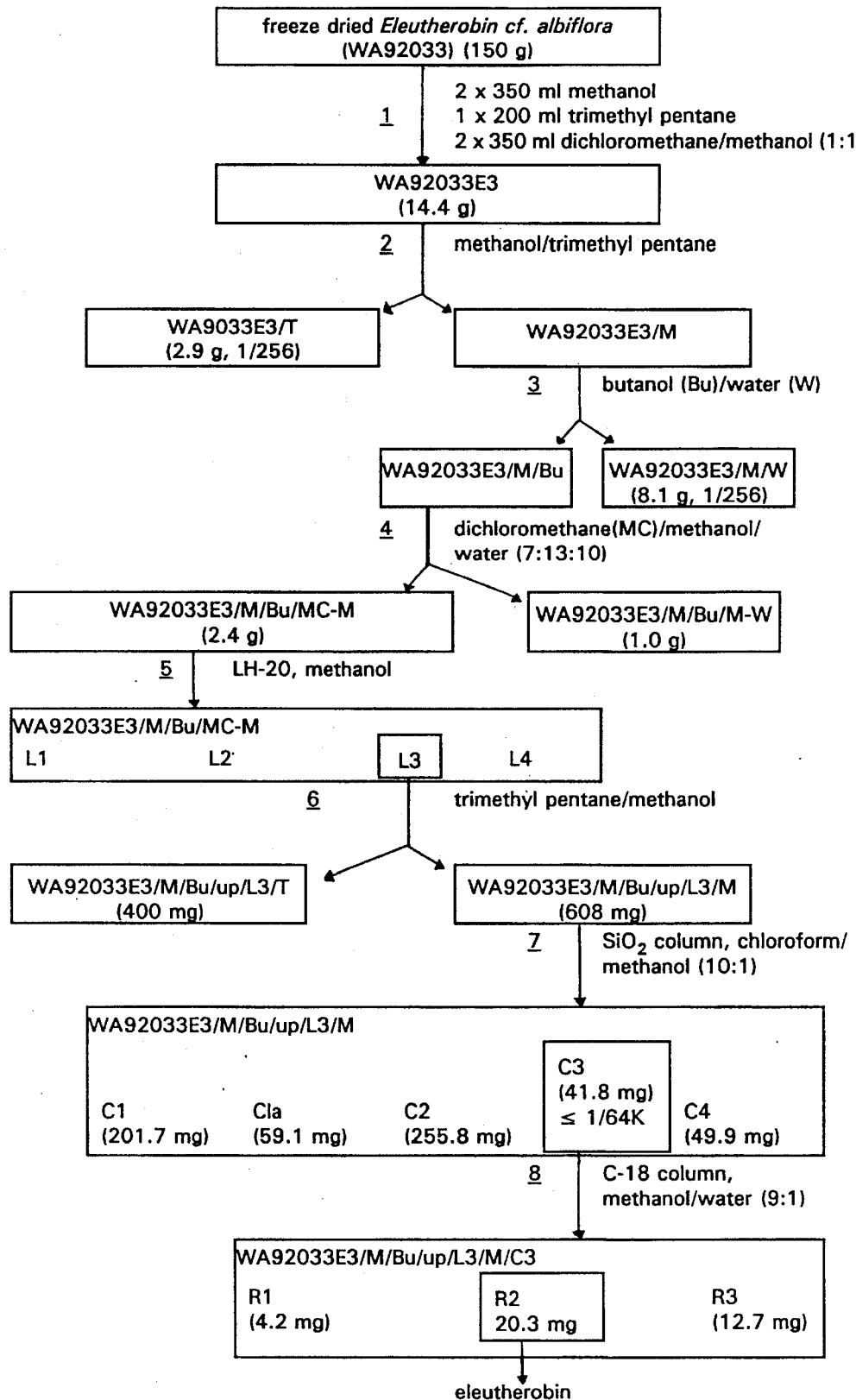
FIG. 5 is a schematic diagram of an exemplary separation scheme for isolating eleutherobin from Eleutherobia spp.

An exemplary procedure for isolating eleutherobin from one of the Eleutherobia species located in Western Australia is set forth schematically in FIG. 5. The isolation procedure is an eight step protocol which involves using conventional separation procedures to isolate eleutherobin from a freeze dried sample of the animal (WA92033). In step 1, the freeze dried sample is extracted sequentially with methanol, trimethyl pentane and dichloromethane/methanol(1:1). In step 2, the extract (WA92033E3) is subjected to solvent partitioning in methanol/trimethyl pentane. In step 3, the methanol fraction from step 2 (WA92033E3/M) is further solvent partitioned in butanol/water. In step 4, the butanol fraction from step 3 (WA92033E3/M/Bu) is subjected to a further solvent partition in dichloromethane/methanol/water. In step 5, the dichloromethane/methanol fraction from step 4 (WA92033E3/M/Bu/MC-M) is subjected to size exclusion column chromatography using a Sephadex LH-20 column with methanol solvent. In step 6, the third fraction (L3) isolated in step 5 is subjected to another solvent portion using trimethyl pentane/methanol. In step 7, the methanol fraction from step 6 (WA92033E3/M/Bu/MC-M/L3/M) is subjected to silica gel column chromatography using chloroform/methanol (10:1) eluent. In step 8, the third fraction from step 7 is subjected to reverse-phase high pressure column chromatograph using a reversed-phase C-18 column and methanol/water (9: 1) as the eluent. The second fraction (R$_2$) eluted in step 8 is eleutherobin. As indicated in FIG. 5, the amount of eleutherobin recovered from 150 grams of freeze dried animal will be on the order of 23 mg.

The Eleutherobia species which contain eleutherobin are found off the coast of Western Australia near the city of Exmouth. Two exemplary animals (WA92-033 and WA92-034) are similar to *E. albiflora* (Utinomi) and *E. grayi*, but not identical with the original descriptions provided by Utinomi (H. Utinomi, The Alcyonarian Genus *Bellonella* (*Eleutherobia*) from Japan with Descriptions of Two New Species. Publications of the Seto Marine Biological Laboratory, Vol. VI, No. 2, pages 160–161, December, 1957.). The two species each contain eleutherobin. The specimen most closely related to *E. albiflora* is red, while the specimen similar to *E. grayi* is smaller, yellow in form. Both animals were collected in the same area. Both specimens are cylindrical colonies measuring approximately 50–60 mm in length and 10 mm in diameter. The polyps over the capitulum are fully extended beyond the slightly raised calyces which are irregularly distributed at intervals of ca 1 mm. Each polyp is colorless and lacks spicules. The pinnules are somewhat clavate in shape, terminating to a globose thickening; the longest one located in the middle measures ca. 0.3 mm in length. The exemplary animal which most closely resembles *E. grayi* (WA92-034) possesses sclerites as short as 0.08 mm, which is in contract to the original specimens which possess sclerites measuring 0.18 mm.

Eleutherobin may also be prepared by first isolating sarcodictyin A from *Sarcodictyon roseum* as described in the articles referenced in the BACKGROUND OF THE INVENTION. The sarcodictyin is then selectively reduced (me ester) and glycosylated in accordance with well known procedures used to add an arabinopyranose unit to sarcodictyin which results in the production of eleutherobin (Gaylord, Reduction With Complex Metal Hydrides, *Interscience*, N.Y., 1956, pp. 391–531; and Fieser & Fieser, *Advanced Organic Chemistry*, Rheinhold, N.Y., 1961, pp. 933–937). Eleutherobin may also be synthesized by starting with other known compounds that contain the same diterpene skeleton as eleutherobin.

The present invention also covers analogs of eleutherobin having the formula:

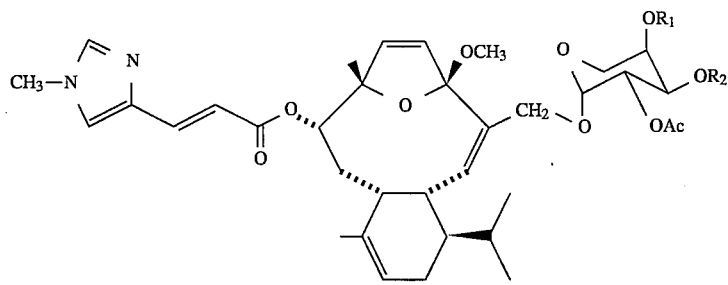

where $R_1$ and $R_2$ are H or acyl groups having from 1 to 6 carbon atoms. These ester analogs of eleutherobin can be prepared by using conventional synthesis procedures in which acyl groups are substituted for the existing hydrogen atoms present at the $R_1$ and $R_2$ positions in eleutherobin. The ester analogs where $R_1$ is methyl and $R_2$ is H or where $R_1$ is H and $R_2$ is methyl are preferred.

Eleutherobin and the above described analogs are useful as cytotoxic agents. The compounds are used in the same manner as other known cytotoxic agents. They may be used alone or in combination with suitable pharmaceutical carriers and other bioactive materials. They are used both in vitro and in vivo to kill a wide variety of cell types. Eleutherobin and its analogs have been shown to be cytotoxic with respect to cancer cells. For example, in vitro toxicity of eleutherobin was tested in the HCT116 human colon carcinoma cell line and a multidrug resistant subline, HCT116/VM46, which overexpresses P-glycoprotein and is over 100-fold resistant to taxol. Eleutherobin was nearly as cytotoxic as taxol in the HCT116 cell line and was 52-fold cross resistant in the HCT116/VM46 subline. The cytotoxicity of eleutherobin was also tested in a human ovarian carcinoma cell line A2780. Eleutherobin was also found to be cytotoxic with respect to the A2780 cell line. The results of the above cytotoxicity assays are set forth in TABLE 5.

TABLE 5

| In vitro Cytotoxicity of Eleutherobin Against Taxol Sensitive and Resistant Human Colon and Ovarian Cell Lines | | | |
|---|---|---|---|
| | $IC_{50}$ (nM)[1] | | |
| | HCT116 | HCT116/VM46 | A2780 |
| paclitaxel (taxol) | 4.6 | 5.37 (117)[2] | 6.7 |
| WHF P 92033 | 10.7 | 554 (52) | 13.7 |

[1] Cytotoxicity was determined after 72 hour exposure by XTT assay.
[2] Value in parenthesis is fold resistance relative to corresponding parent cell line.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

What is claimed is:

1. A composition of matter comprising a compound having the formula:

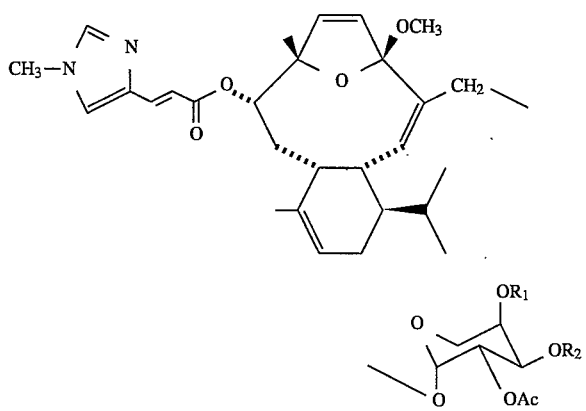

where $R_1$ and $R_2$ are hydrogen or an acyl group having from 1 to 6 carbon atoms.

2. A composition of matter according to claim 1 wherein $R_1$ is hydrogen.

3. A composition of matter according to claim 1 wherein $R_2$ is hydrogen.

4. A composition of matter according to claim 2 wherein $R_2$ is hydrogen.

* * * * *